(12) United States Patent
Peery (10) Patent No.: US 10,195,012 B2
(45) Date of Patent: Feb. 5, 2019

(54) ABDOMINAL WALL CLOSURE DEVICES AND METHODS FOR USE THEREOF

(71) Applicant: Sanford Health, Sioux Falls, SD (US)

(72) Inventor: Curtis Peery, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 1 day.

(21) Appl. No.: 15/430,015

(22) Filed: Feb. 10, 2017

(65) Prior Publication Data

US 2017/0231740 A1 Aug. 17, 2017

Related U.S. Application Data

(60) Provisional application No. 62/294,512, filed on Feb. 12, 2016.

(51) Int. Cl.
| | | |
|---|---|---|
| *A61B 17/08* | (2006.01) | |
| *A61F 2/00* | (2006.01) | |

(Continued)

(52) U.S. Cl.
CPC ........ *A61F 2/0063* (2013.01); *A61B 17/0401* (2013.01); *A61B 17/064* (2013.01);
(Continued)

(58) Field of Classification Search
CPC .... A61F 2/0063; A61F 2/0077; A61F 2/0811; A61F 2002/0068; A61F 2002/0072; A61F 2002/009; A61F 2002/0086; A61F 2002/0817; A61F 2250/0097; A61F 2250/0031; A61F 2210/0076; A61F 2220/0008; A61F 2220/0075; A61F 2220/033; A61F 2220/0083; A61F 2230/0067; A51F 2230/0008; A61B 17/0401; A61B 17/08; A61B 17/0057; A61B 17/0644; A61B 17/10; A61B 17/0466; A61B 17/0469; A61B 17/0487;
(Continued)

(56) References Cited

U.S. PATENT DOCUMENTS 5,571,139 A * 11/1996 Jenkins, Jr. ........ A61B 17/0401
606/232
5,695,525 A * 12/1997 Mulhauser ............ A61F 2/0063
600/37

(Continued)

FOREIGN PATENT DOCUMENTS

| EP | 2649961 A1 | 10/2013 |
| WO | 10/078591 A1 | 7/2010 |

OTHER PUBLICATIONS

International Search Report for corresponding PCT application No. PCT/US2017/017439, dated May 11, 2017.

*Primary Examiner* — Elizabeth Houston
*Assistant Examiner* — Mohamed Gabr
(74) *Attorney, Agent, or Firm* — McDonnell Boehnen Hulbert & Berghoff LLP (57) ABSTRACT

The present disclosure provides a wound closure device that includes (a) a biocompatible material configured to be brought into abutment with a tissue surface, and (b) a plurality of fixation components connected to and extending through the biocompatible material, where at least one of the plurality of fixation components is configured to allow a suture to be connected to and extend through the at least one fixation component.

18 Claims, 9 Drawing Sheets

(51) Int. Cl.
*A61B 17/04* (2006.01)
*A61B 17/064* (2006.01)

(52) U.S. Cl.
CPC . *A61B 2017/044* (2013.01); *A61B 2017/0427* (2013.01); *A61B 2017/0458* (2013.01); *A61B 2017/0464* (2013.01); *A61B 2017/0495* (2013.01); *A61B 2017/0647* (2013.01); *A61B 2017/0648* (2013.01); *A61B 2017/0649* (2013.01); *A61F 2002/0068* (2013.01); *A61F 2002/0072* (2013.01); *A61F 2210/0076* (2013.01); *A61F 2220/0008* (2013.01); *A61F 2220/0016* (2013.01); *A61F 2250/0067* (2013.01)

(58) Field of Classification Search
CPC .. A61B 2017/0464; A61B 2017/00004; A61B 2017/081
See application file for complete search history.

(56) References Cited

U.S. PATENT DOCUMENTS

| | | | |
|---|---|---|---|
| 2006/0116718 A1* | 6/2006 | Leiboff | A61B 17/0401 606/228 |
| 2006/0252980 A1* | 11/2006 | Arnal | A61B 17/0401 600/29 |
| 2006/0276841 A1* | 12/2006 | Barbieri | A61B 17/0401 606/232 |
| 2007/0299538 A1* | 12/2007 | Roeber | A61F 2/0063 623/23.72 |
| 2009/0082792 A1 | 3/2009 | Koyfman | |
| 2010/0018976 A1 | 7/2010 | Thomas | |
| 2010/0168505 A1* | 7/2010 | Inman | A61B 17/0401 600/30 |
| 2012/0259348 A1* | 10/2012 | Paul | A61F 2/0063 606/151 |
| 2013/0211193 A1 | 8/2013 | Alexander | |

* cited by examiner

ABDOMINAL WALL CLOSURE DEVICES AND METHODS FOR USE THEREOF

RELATED APPLICATIONS

This application claims the benefit of priority to U.S. Provisional Application No. 62/294,512 entitled "Abdominal Wall Closure Devices and Methods," filed on Feb. 12, 2016, the contents of which are hereby incorporated by reference in their entirety.

BACKGROUND THE INVENTION

Abdominal surgery is required both for diagnostic and interventional techniques within the abdominal cavity. A midline incision is preferred in many cases as it allows for wide access to most of the abdominal cavity. Such a midline incision is a vertical one along the linea alba which connects the left and right side rectus muscles. After the procedure, the midline incision must be closed. While re-approximating the left and right abdominal wall, many techniques can be used to secure them together. One such technique is a layered closure. The layered closure allows for individual layers to be re-approximated and sewn sequentially. The benefit to this approach is that there are multiple lines of suture creating a built-in redundancy. If one suture line breaks, there are other sutures still holding layers of the abdominal wall together. The downside of this technique is that multiple suture lines may have variable degrees of tension. Localized areas of increased tension can create localized areas of tissue necrosis which can put the closure at risk of not healing and ultimately failing. An alternative technique is a mass closure. Mass closures re-approximate the abdominal wall with a single continuous suture. The mass closure approach has the advantage of maintaining consistent pressures throughout. However, if the sole suture line breaks the entire closure will fail.

If a midline incision closure fails it can be devastating. If a hernia forms, that means the closure partially failed and soft tissue extends through the muscular layer creating a bulge of soft tissue. This can cause multiple complications such as strangulation of the bowel, and therefore such hernias need to be repaired. In some instances, there is a defect in both the abdominal muscle and skin. This is known as abdominal wall dehiscence. This is a dangerous condition that has to be repaired and results in death in 30% of patients. If an organ, such as the bowel, extends through the muscle and skin it is known as evisceration. This is an extremely critical condition and needs to be repaired immediately. Risk factors for dehiscence and evisceration are age, collagen disorder, diabetes, obesity, and poor closure techniques. When a midline closure fails, it is often repaired with retention sutures. Retention sutures are reinforced sutures with a tubular structure through which the suture passes that can be partially embedded within the muscular layer. Retention sutures are not preferable in that they do not allow natural healing of the abdominal wall and can cause long term defects.

Recently, surgical meshes have been introduced to reinforce midline incisions to prevent hernia, dehiscence, and evisceration formation. They are placed under the rectus muscle and are sewn to the soft tissue. After the surgical mesh is in place, the overlying layers can be re-approximated and sewn in a traditional manner. While these surgical meshes have shown promise in preventing poor outcomes, they are challenging to put in place. They require additional sutures to be placed which increases procedure time. They also can adhere to themselves or nearby soft tissues. They also require sutures to be placed within the abdominal cavity which requires very difficult surgical maneuvers to be effective. Because of these drawbacks, many surgeons do not elect to place the beneficial and prophylactic surgical meshes. An easier technique would ensure more surgeons would elect to place the meshes resulting in fewer complications. It would also reduce the amount of time to complete the procedure, which would result in significant monetary savings within the health care system. As such, an improved abdominal wall closure device may be desirable.

SUMMARY OF THE INVENTION

Thus, in one aspect, the present disclosure provides a wound closure device that includes (a) a biocompatible material configured to be brought into abutment with a tissue surface, and (b) a plurality of fixation components connected to and extending through the biocompatible material, where at least one of the plurality of fixation components is configured to allow a suture to be connected to and extend through the at least one fixation component.

In another aspect, the present disclosure provides a method of closing a wound in a tissue, the method includes (a) positioning a wound closure device into abutment with an interior surface of the tissue at the location of the wound, wherein the wound closure device comprises (i) a biocompatible material, and (ii) a plurality of fixation components connected to and extending through the biocompatible material, where at least one fixation component of the plurality of fixation components is configured to allow a suture to be connected to and extend through the at least one fixation component, (b) threading the suture through the tissue from the interior surface of the tissue to an exterior surface of the tissue at the location of the wound, and (c) applying a force to the wound closure device such that at least one fixation component pierces the interior surface of the tissue, thereby affixing the wound closure device to the interior surface of the tissue.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means +/−5%.

As used herein, "abdominal wall" means the boundary of the abdominal cavity comprised of skin, subcutaneous fat, three layers of muscle, parietal peritoneum, extracorporeal fat, fascia, and the rectus sheath.

As used herein, "midline incision" means a vertical incision which follows the linea alba. Midline incisions are particularly favored in diagnostic laparotomy, as they allow wide access to most of the abdominal cavity.

As used herein, "layered closure" means a sequential closure of each fascia layer individually. This technique allows for redundancy because of multiple layers being fixed with suture by multiple suture lines.

As used herein, "mass closure" means a continuous fascia closure with a single suture. This technique allows for even tension distribution along the suture minimizing the risk of tissue strangulation, preventing tissue necrosis and suture failure. However, there are no redundancies in this closure technique.

As used herein, "suture" means a stitch or row of stitches holding together the edges of a surgical incision.

As used herein, "retention suture" means a heavy reinforcing suture placed deeply within the muscles and fascia of the abdominal wall intended to relieve tension on the primary suture line and avoid post-surgical wound disruption.

As used herein, "ventral incisional hernia" means a bulge of tissues through an opening or defect within the abdominal wall muscles. Ventral incisional hernia often occur at the site of past surgical incisions where the skin has become weak or thin.

As used herein, "abdominal wall dehiscence" means a surgical complication in which a closure ruptures along the surgical incision. Abdominal wall dehiscence has a 30% risk of death.

As used herein, "abdominal wall evisceration" means an extrusion of viscera outside of the body through a ruptured surgical incision.

As used herein, "surgical mesh" means loosely woven sheet or a solid film which is used as either a permanent or temporary support for a midline incision upon closure. A surgical mesh can be created from inorganic, organic, biological materials or a combination thereof.

As used herein, "underlay mesh" means a mesh which is placed posterior to the posterior layer of the rectus sheath and is attached to the rectus sheath or other nearby soft tissues as a means of reinforcing the closure line.

As used herein, "fixation component" means a single use device used to fix the biocompatible material to the soft tissue such as the rectus sheath.

As used herein, "biocompatible material" means any suitable biocompatible material, either synthetic or biologic, such as titanium, nitinol, polypropylene, polyethylene terephthalate (PET), Poly-4-hydroxybutyrate (P4HB) and Polytetrafluoroethylene (PTFE).

As used herein, "inferior glue" means a glue that creates a nonpermanent reusable mechanical connection between two surfaces.

With reference to the Figures, the present disclosure provides a wound closure device 100 according to embodiments. The wound closure device 100 may be used to close or repair a midline incision. The wound closure device 100 may take the place of or be used in combination with sutures, staples or other common closure devices. In addition, the wound closure device 100 may serve as a scaffolding, a replacement for, or to strengthen an affected tissue surface, such as the abdominal wall. For example, the wound closure device 100 may be used in abdominal surgery, such as in the repair of hernias and other fascial deficiencies. In particular, the wound closure device 100 may be used to close abdominal wounds having a high risk of dehiscence and evisceration and incisional hernia. Further, the wound closure device 100 may be used in either the underlay or recto-rectus positions, as described in additional detail below.

Figure 1:
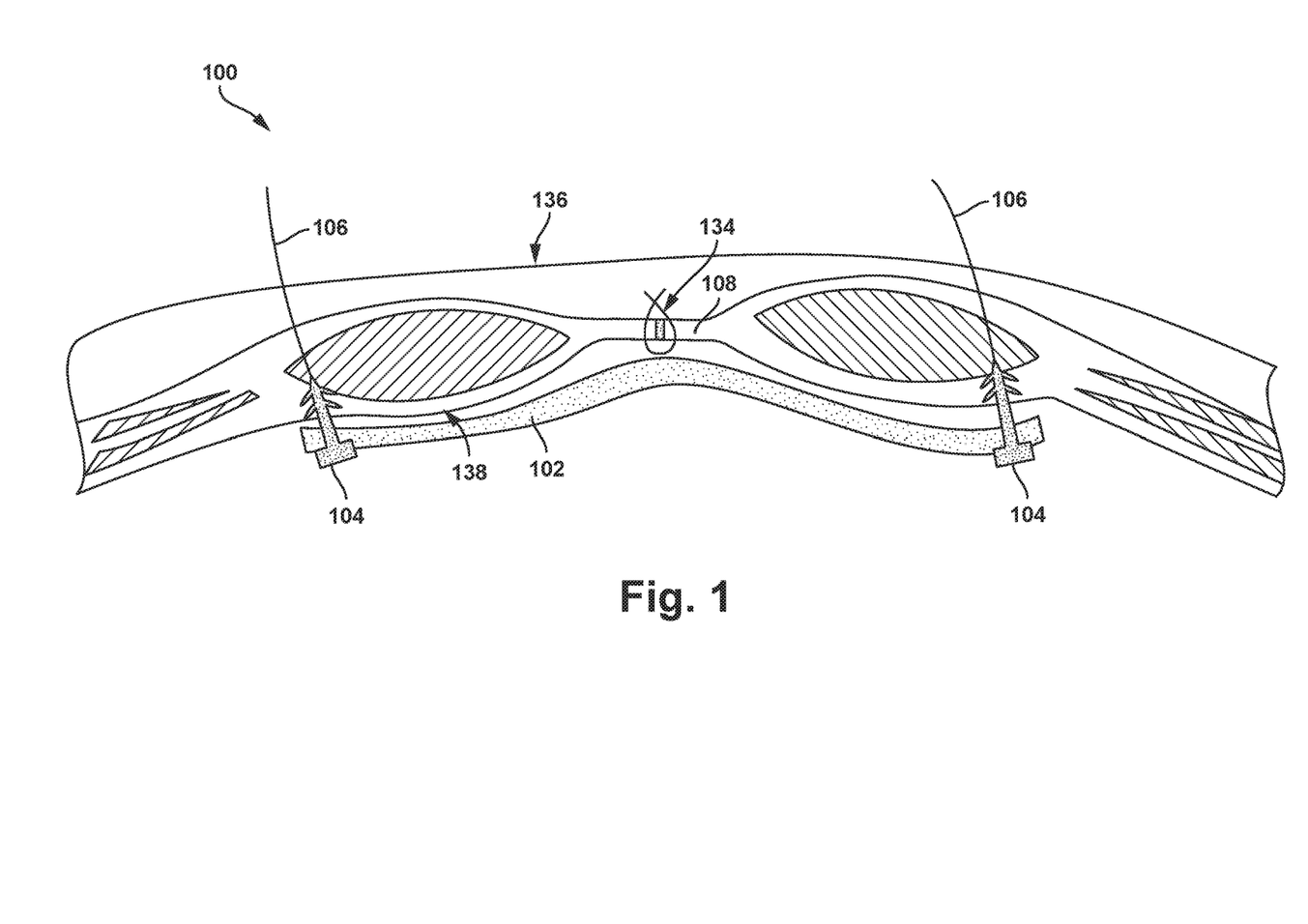
FIG. 1 is a side cross-section view of a wound closure device, according to an example embodiment.

In particular, FIG. 1 illustrates a wound closure device 100 according to an example embodiment. As shown in FIG. 1, the wound closure device 100 includes a biocompatible material 102. The wound closure device 100 also includes a plurality of fixation components 104 connected to and extending through the biocompatible material 102. At least one of the plurality of fixation components 104 is configured to allow a suture 106 to be connected to and extend through the at least one fixation component 104.

The biocompatible material 102 may be made of any biocompatible material, including bioinert materials, suitable for introduction into a living body. Generally, the biocompatible material 102 is configured to be brought into abutment with a tissue surface 108 requiring repair or closure. For example, the biocompatible material 102 may be fabricated from a woven type material, such as a mesh (described in additional detail below), or a solid material. In either case, the biocompatible material 102 may include a number of pores or holes to allow for tissue ingrowth and the passage of fluid. Further, the biocompatible material 102, which may be provided as a mesh, may also be capable of eluting one or more drugs or agents into the tissue. One or more drugs or agents may be coated on or impregnated in (e.g., loaded in the pores of the mesh) the biocompatible material 102 material.

The shape, size, thickness and other characteristics of the biocompatible material 102 may be selected based on the size, shape and type of wound to be closed, the needs or limitations of the patient, or surgeon preference, among other things. In some examples, the biocompatible material 102 may be provided in a predetermined shape. Alternatively, the biocompatible material 102 may be provided as a sheet of material capable of being cut to size by a surgeon.

The biocompatible material 102 may be provided as a mesh. The mesh may be absorbable, partially absorbable (bioactive), or non-absorbable (permanent and bioinert) and made of any suitable biocompatible material, either synthetic or biologic, such as titanium, nitinol, polypropylene, polyethylene terephthalate (PET), Poly-4-hydroxybutyrate (P4HB) and Polytetrafluoroethylene (PTFE). Additionally, the mesh may be flexible and, in some cases, stretchable to conform to the shape of a tissue surface. Composite meshes, or multilayer meshes, combining different materials may also be used. For example, as will be discussed further below, a composite mesh including a layer of polypropylene woven mesh and a layer of a microreplicated material may be used. The pore and filament size of the mesh may be customized or selected based on the needs of the patient or surgeon preference. A mesh having a higher porosity may promote faster and more extensive tissue integration. For example, in some cases, a thin filament, large pore construction mesh may be selected. The mesh can be woven, or it can be a solid film or sheet that can then have holes or apertures cut into it with or without a microreplicated surface.

In some embodiments, the mesh is a microreplicated mesh. A "microreplicated" material may include any material that is self-fixating and/or increases friction so as to prevent sliding of the biocompatible material 102 along the tissue surface. An exemplary "microreplicated" mesh includes a mesh having a plurality microgrips made of monofilament polylactic acid (PLA). Reducing or prohibiting movement between the biocompatible material 102 and the tissue surface may encourage pervasive and faster tissue ingrowth into the biocompatible material 102, thereby speeding wound healing and recovery of the patient. Further, the microreplicated surface may provide stability to the wound area, further reducing the occurrence of incisional hernia, dehiscence and evisceration. The microreplicated mesh may, in one example, be designed such that the mesh material itself forms a microreplicated surface and there are no added components to the mesh. In another embodiment, the microreplicated mesh is constructed from a separate microreplicated material that is printed or onlayed onto the mesh surface. The replicated material can range in size and form. A multilayer mesh may include a composite mesh having more than one layer of the same or different materials. In one example, the multilayer mesh may include a typical surgical mesh with a layer of microreplicated material coated, applied or laminated thereto. Moreover, the multilayer mesh may comprise some absorbable and some non-absorbable materials. The mesh may be used for both contaminated and noncontaminated wounds.

Figure 2A:
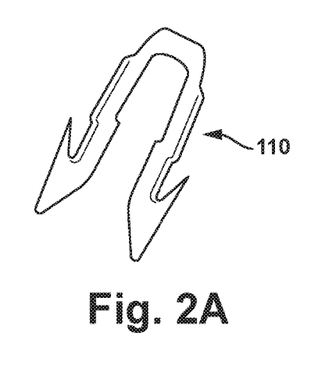
FIG. 2A is a perspective view of an example fixation component, according to an example embodiment.
Figure 2B:
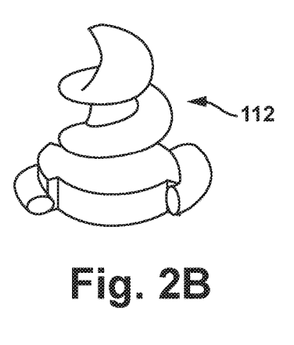
FIG. 2B is a perspective view of an example fixation component, according to an example embodiment.
Figure 2C:
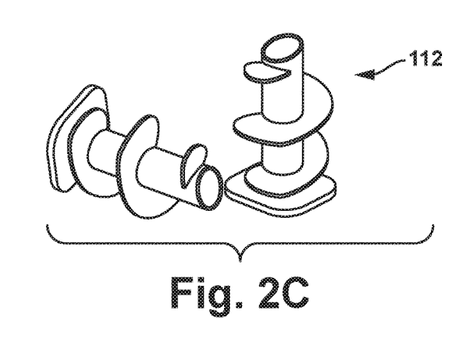
FIG. 2C is a perspective view of an example fixation component, according to an example embodiment.

The plurality of fixation components 104 embedded in the biocompatible material 102 may be used to affix the biocompatible material 102 to the tissue surface 108. Each fixation component 104 may include any device or structure capable of penetrating the tissue surface 108 and securing the biocompatible material 102 thereto. In one example, the fixation component 104 may be in the form of a staple-like device 110, as shown in FIG. 2A. Alternatively, the fixation component 104 may be a tack 112. The tack 112 may be provided in a number of various shapes and sizes, as shown in FIGS. 2B-2E. Other shapes are contemplated.

Figure 2D:
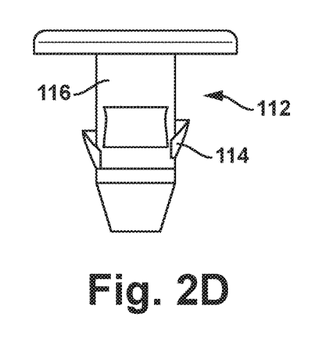
FIG. 2D is a side view of an example fixation component, according to an example embodiment.
Figure 2E:
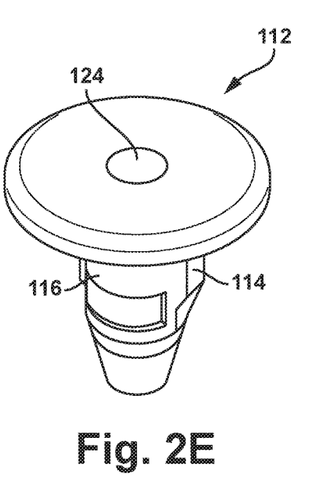
FIG. 2E is a perspective view of an example fixation component, according to an example embodiment.

In some embodiments, each of the plurality of fixation components 104 may include at least one protrusion 114 configured to penetrate the tissue surface 108. The protrusion 114 may be in the form of a barb extending from the body 116 of the fixation component 104 and may be angled to prevent pull-out of the fixation component 104 from the tissue surface 108. In one example, a plurality of protrusions of uniform shape are positioned in a staggered formation around the body and angled away from the distal tip of the fixation component. This example is shown in FIGS. 2D and 2E, where the fixation component 104 is a tack 112. The at least one protrusion 114 may also comprise one or more sutures 106 disposed on the center column of the tack 112. The sutures 106 could be passed from the inner side of the abdominal wall to the outer side, then tied outside the tissue surface 108 of the patient to hold the biocompatible material 102 in place. Other numbers, shapes and configurations of the protrusions are contemplated.

The biocompatible material 102 may be fabricated together such that the fixation components 104 and biocompatible material 102 are formed as a continuous material. Alternatively, the fixation components 104 and the biocompatible material 102 may be fabricated separately, such that the fixation components 104 are subsequently secured to the biocompatible material 102 prior to the surgery or in manufacture. In this case, the fixation components 104 and the biocompatible material 102 may be formed from two different materials. For instance, the biocompatible material 102 may be made of a non-biodegradable material while the fixation components 104 are made of a biodegradable material. Generally, the fixation components 104 may be formed from any suitable biocompatible materials, for example, resorbable poly (D, L)-lactide (PLA). The plurality of fixation components 104 may be attached to the biocompatible material 102 in any number of arrangements. For example, the fixation components 104 may be positioned in regular intervals at the periphery of the biocompatible material 102, as shown in FIG. 3.

Figure 3:
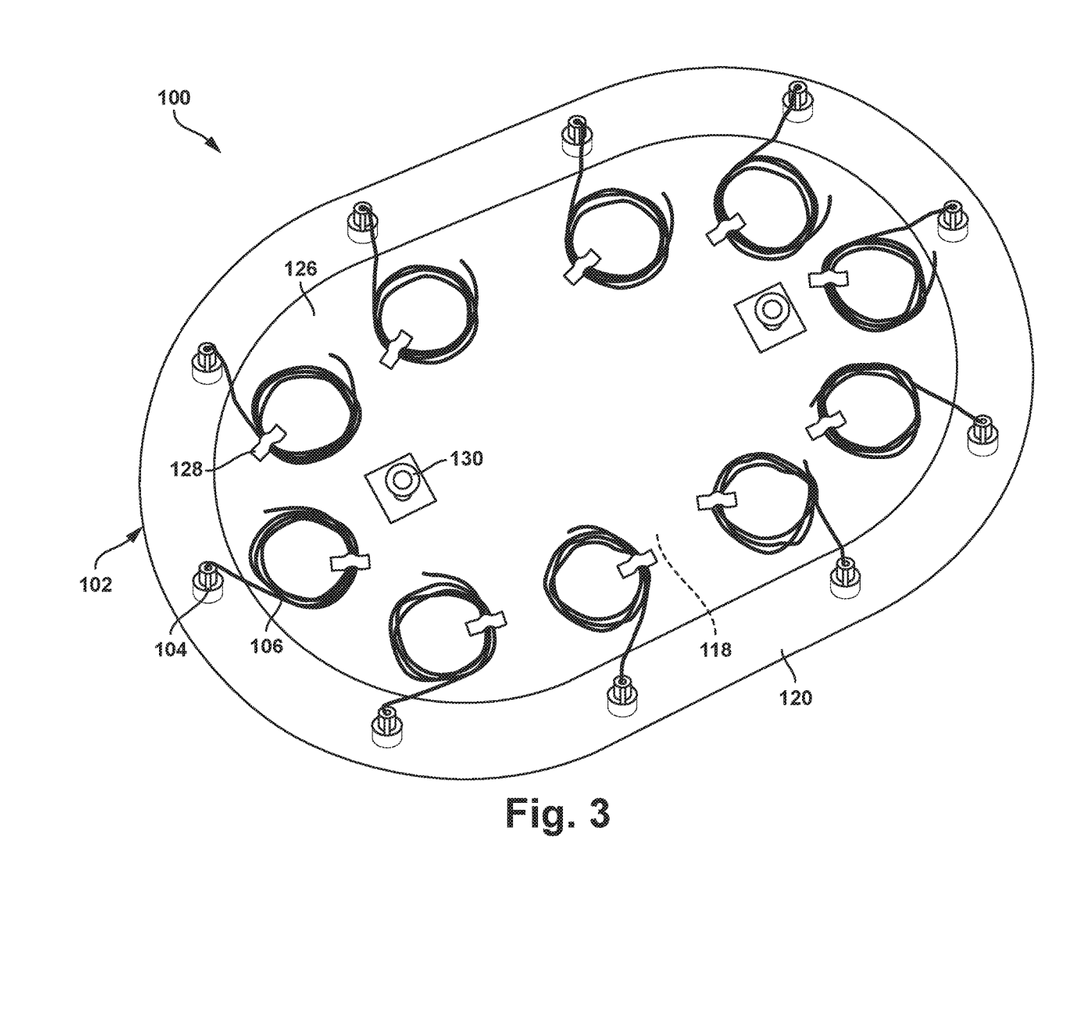
FIG. 3 is a top perspective view of a wound closure device, according to an example embodiment.

In some examples, as shown in FIG. 3, the biocompatible material 102 may comprise at least two portions—an inner portion 118 surrounded by an outer portion 120. The plurality of fixation components 104 may be connected to the outer portion 120. The inner portion 118 may comprise a first material, and the outer portion 120 may comprise a second material that is different than the first material. For example, the outer portion 120 may be provided as a generally rigid and solid material to provide structural support for the fixation components and to the wound closure device 100 as a whole, while the inner portion 118 may comprise a mesh, as described above.

As discussed above, one or more of the fixation components 104 in the plurality are configured to allow a suture 106 to be connected to and extend therethrough. The wound closure device 100 need not be provided with a suture 106 already connected to and extending through the one or more fixation components 104. In one example, a first end of the suture(s) 106 may be coupled to a given fixation component 104 of the plurality of fixation components, and a second end of the suture(s) may be coupled to a needle or other piercing member 122. In operation, the needle or other piercing member 122 may be used to thread the suture 106 through the intended tissue and pull the wound closure device 100 into abutment with the tissue surface 108 and cause the fixation components 104 to penetrate the tissue surface 108. In another embodiment, a suture 106 may be embedded into one or more of the plurality of fixation components 104 in the biocompatible material 102, for example, during fabrication of the fixation component 104 or fabrication of the biocompatible material 102, if the fixation component 104 is integral thereto.

In one embodiment, the suture 106 may be connected to one or more of the plurality of fixation components by inserting a length of suture through an axial hole 124 in the one or more fixation components 104 and securing the suture 106, for example, by means of a knot. The diameter of the axial hole 124 may be selected to accommodate a variety of known suture gauges. In some examples, the wound closure device 100 may include a suture 106 pre-loaded into one or more of the plurality of fixation components 104.

In operation, the suture 106 may be threaded, via a needle or other piercing device 122, through the tissue surface 108. By applying a tension to the suture 106, the one or more fixation components 104 are pulled in the direction of and caused to pierce the tissue surface 108, thereby affixing the wound closure device to the tissue surface 108.

The wound closure device 100 may be provided with a deployment plate 126 to facilitate introduction of the device 100 into the body and positioning with respect to the intended tissue surface 108. In one example, an adhesive is positioned on the biocompatible material 102 on the surface contacting the deployment plate 126. In such an example, the deployment plate 126 acts to shield the portion of the biocompatible material 102 covered in an adhesive material from adhering to or otherwise interfering with an unintended tissue surface. Once the biocompatible material 102 is in the desired position, the deployment plate 126 may be removed, exposing the adhesive material, which can thereby be brought into abutment with the intended tissue surface 108. In one example, the adhesive comprises a microreplicated mesh or includes a microreplicated surface of the biocompatible material 102.

In some cases, the deployment plate 126 may provide structural stability or rigidity to, or aid in manipulation of the biocompatible material 102 during implantation. In particular, the deployment plate 126 may aid in pressing the fixation components 104 through the tissue by providing a rigid plane by which all of the fixation components 104 can be pressed through the tissue simultaneously.

Additionally or alternatively, in embodiments where the biocompatible material 102 comprises a microreplicated mesh or includes a microreplicated surface, the deployment plate 126 may serve to cover the microreplicated mesh or surface during insertion and positioning within the body to prevent the biocompatible material 102 from adhering to or becoming caught on an unintended tissue surface 108. The deployment plate 126 may be made of any biocompatible or bioinert material and may be smooth in nature. The shape and size of the deployment plate 126 may be selected to configure to the general shape and size of the biocompatible material 102. In some cases, the deployment plate 126 may be shaped and sized so as to not cover the fixation components 104 extending through the biocompatible material 102, as shown in FIG. 3. The deployment plate may be removably disposed over the biocompatible material 102 using an inferior glue or other adhesive. In another example, a physical element, such as a circular suture, deformable rivet, or other connector extending through both the biocompatible material 102 and the deployment plate 126 may also be used.

In some examples, the deployment plate 126 may include one or more structures 128 or elements for removably securing any suture(s) 106 connected to the fixation component(s) 104 during insertion into the body and positioning in abutment with the intended tissue surface 108. These structure(s) 128 may aid the surgeon in keeping track of the multiple sutures. In one example, the structure(s) 128 comprise tape, as shown in FIG. 3. Other structure(s) for removably securing the suture(s) 106 to the deployment plate 126 are possible as well.

Figure 4:
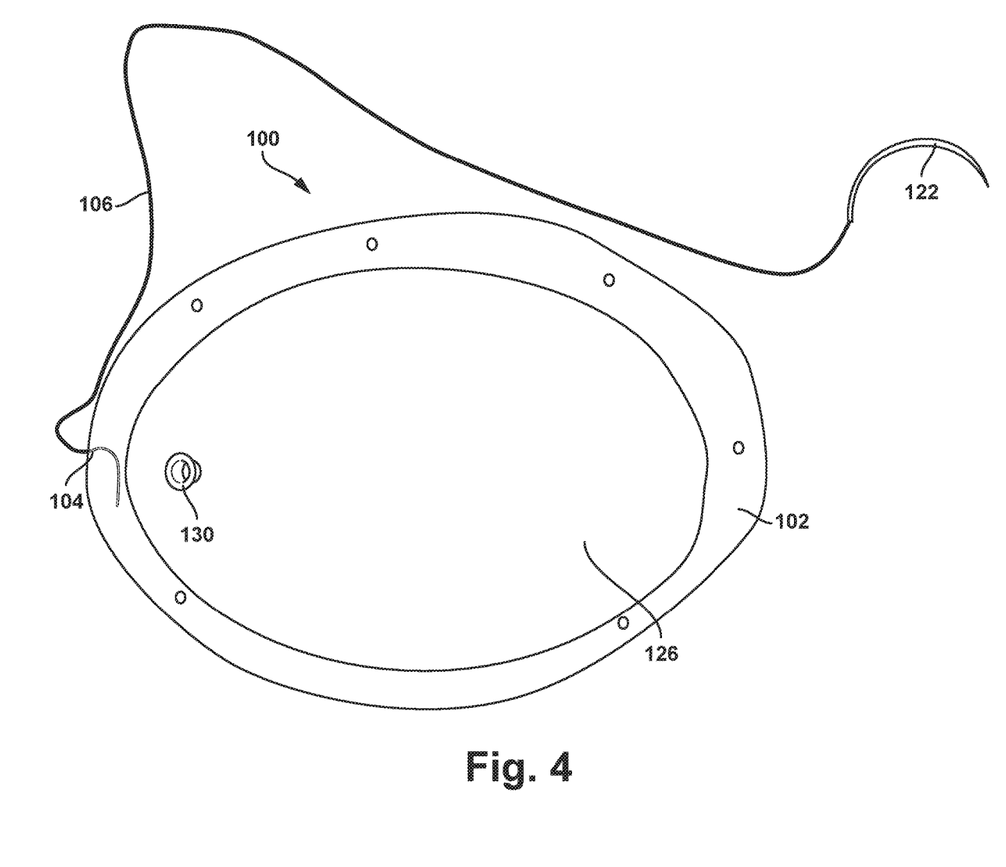
FIG. 4 is a top view of a wound closure device, according to an example embodiment.
Figure 5:
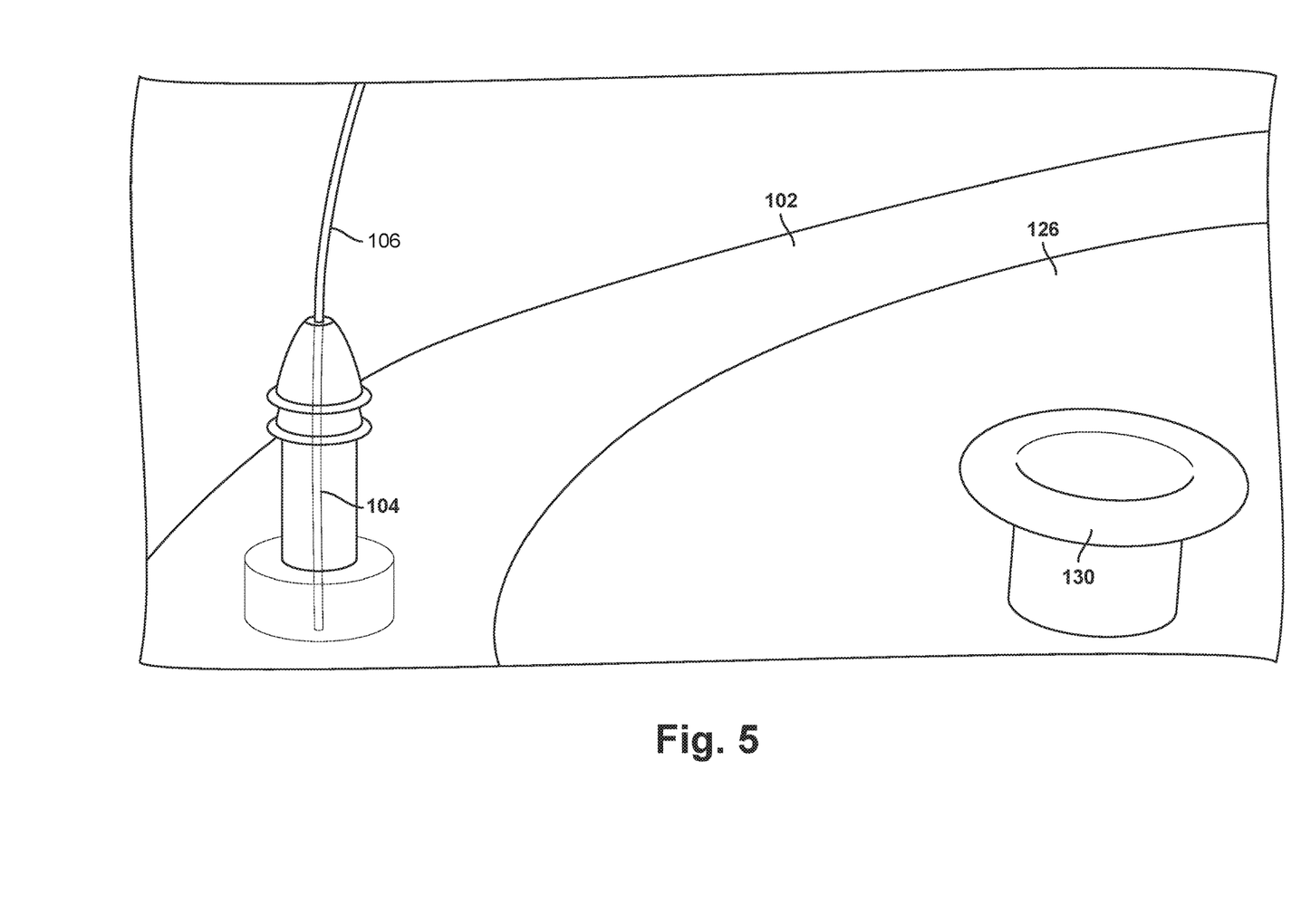
FIG. 5 is a perspective view of an example fixation component positioned through a biocompatible material, according to an example embodiment.
Figure 6:
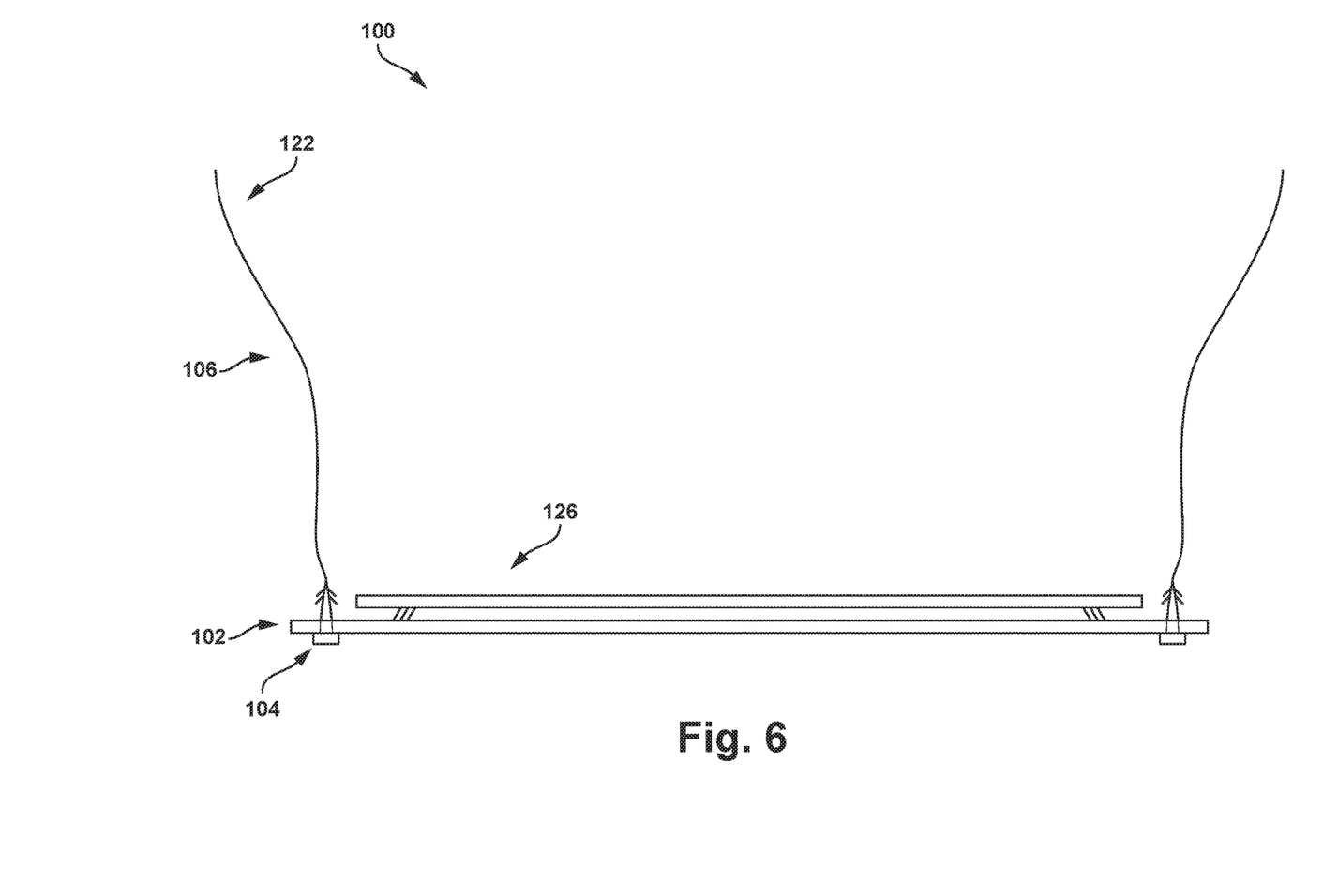
FIG. 6 is a side view of a wound closure device, according to an example embodiment.

In addition, deployment plate 126 may include one or more vertically extending components 130, which extend vertically from the surface of the deployment plate 126. These vertically extending component(s) 130 may be used to pull the deployment plate 126 off of the biocompatible material 102 when the wound closure device 100 is properly positioned. In addition, the vertically extending component(s) 130 may include a hole, as shown in FIGS. 3-5. In such an example, the suture(s) 106 may be positioned in the hole of the vertically extending component(s) 130 to thereby removably secure the suture(s) 106 to the deployment plate 126. In another example, each suture 106 of has a corresponding vertically extending component 130.

In one embodiment, the wound closure device 100 includes a biocompatible material 102, and a plurality of fixation components 104 connected to and extending through the biocompatible material 102. In one example, the plurality of fixation components 104 are not configured to allow a suture 106 to be connected to and extend through the fixation components 104. In such an example, the piercing component of the plurality of fixation components 104 alone is used to affix the wound closure device 100 to the tissue surface 108.

In another embodiment, the wound closure device 100 includes a biocompatible material 102, and a plurality of sutures 106 connected to and extending through the biocompatible material 102. In such an example, the plurality of sutures 106 are configured to pierce the tissue surface 108 to thereby affix the wound closure device 100 to the tissue surface 108.

In yet another embodiment, the wound closure device 100 includes a biocompatible material 102, and a deployment plate 126 to facilitate introduction of the device 100 into the body and positioning with respect to the intended tissue surface 108. In such an example, the wound closure device 100 may not include any fixation components 104 or sutures 106. Instead, an adhesive is positioned on the biocompatible material 102 on the surface contacting the deployment plate 126. In such an example, the deployment plate 126 acts to shield the portion of the biocompatible material 102 covered in an adhesive material from adhering to or otherwise interfering with an unintended tissue surface. Once the biocompatible material 102 is in the desired position, the deployment plate 126 may be removed, exposing the adhesive material, which can thereby be brought into abutment with the intended tissue surface 108 to thereby affix the wound closure device 100 to the tissue surface 108.

Figure 7:
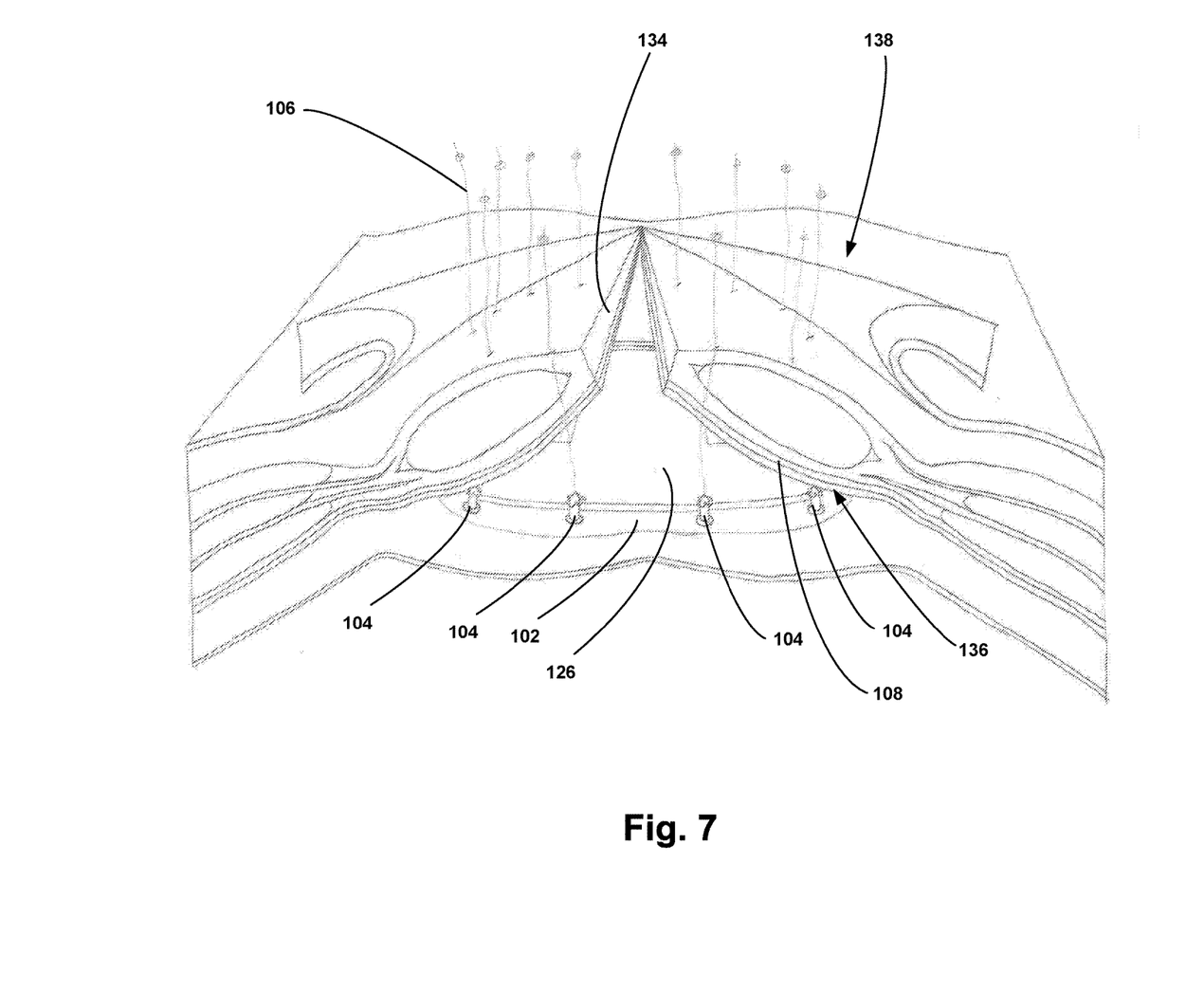
FIG. 7 is a side cross-section view of a wound closure device being positioned in abutment with an interior surface of the tissue at the location of the wound, according to an example embodiment.
Figure 8:
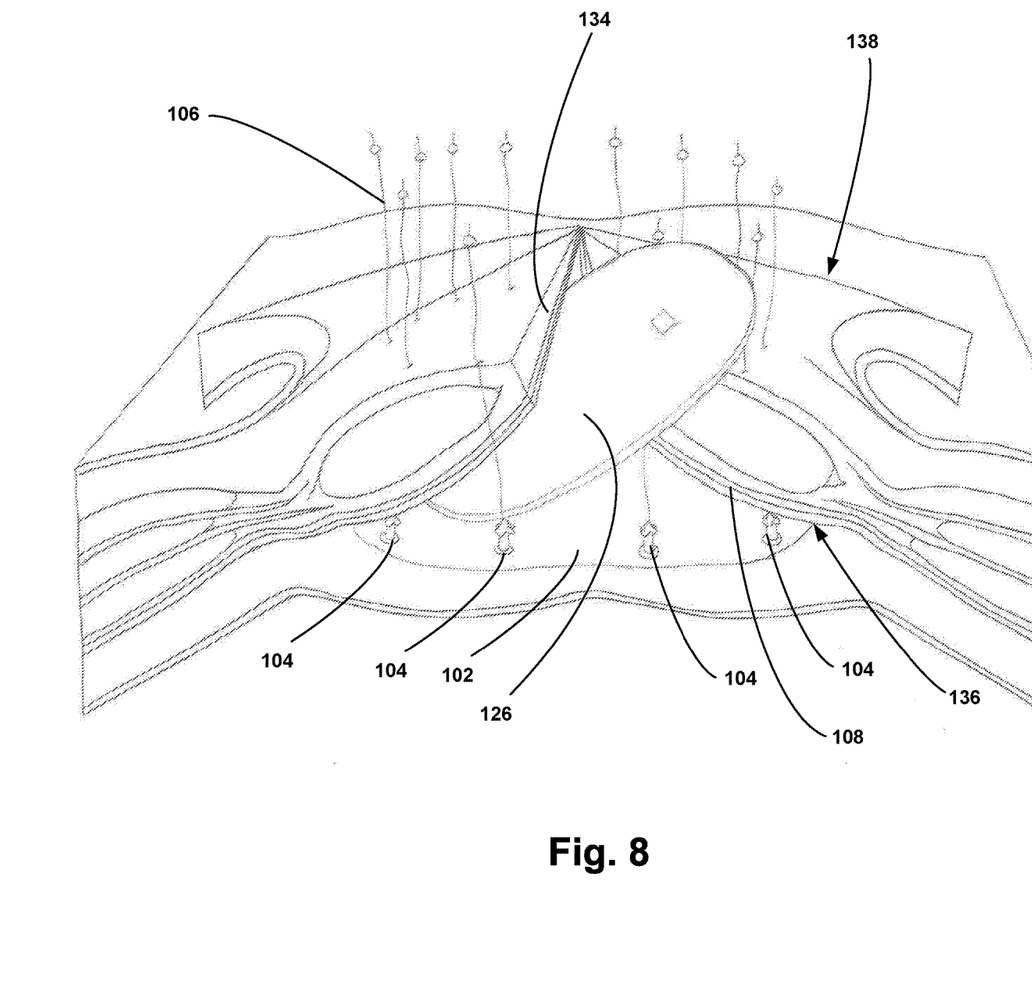
FIG. 8 is a side cross-section view of the deployment plate being removed from the wound closure device of FIG. 7, according to an example embodiment.
Figure 9:
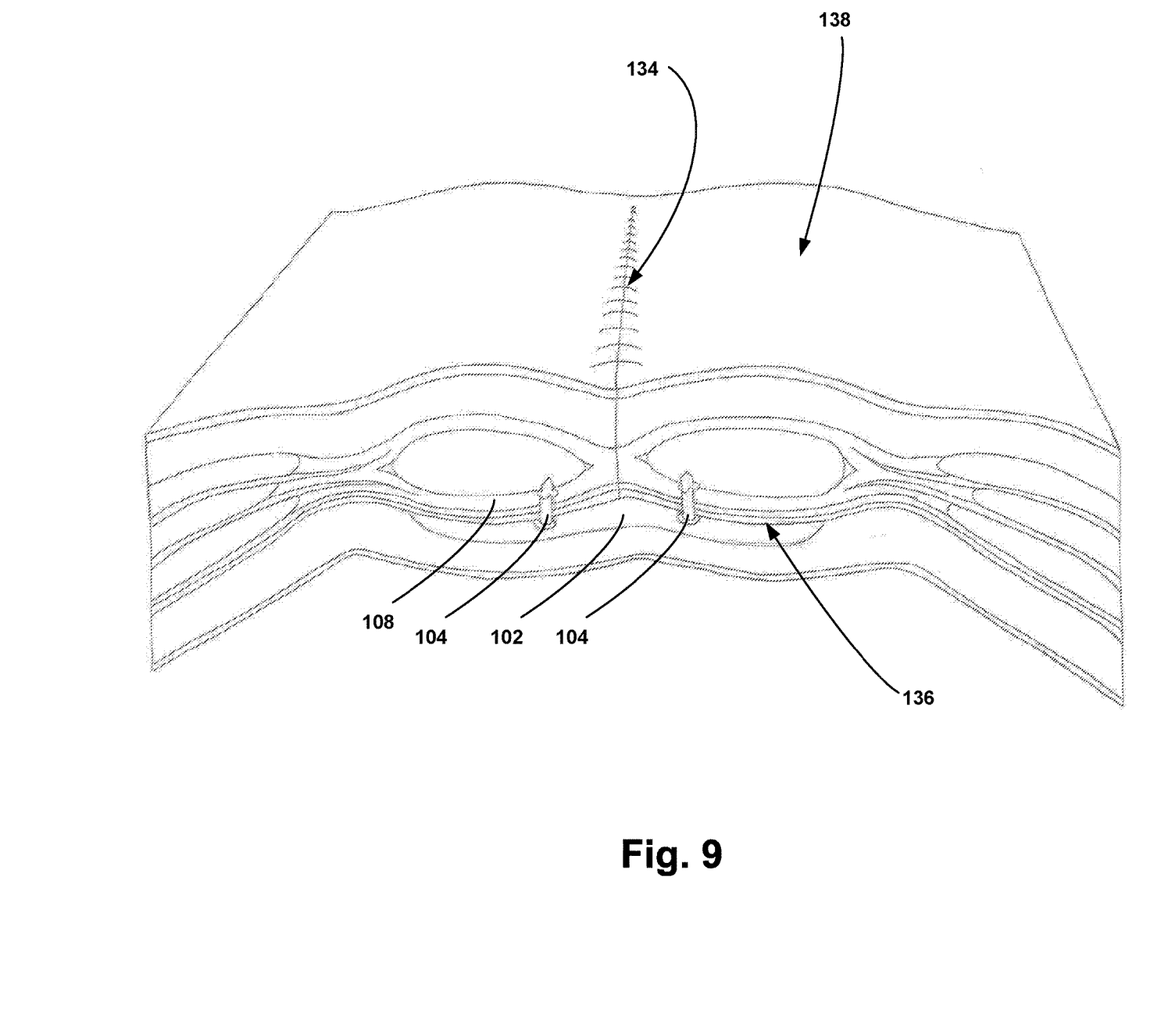
FIG. 9 is a side cross-section view of the wound closure device of FIG. 7 positioned in the abdominal cavity after the wound is sewn, according to an example embodiment.

The method of using the wound closure device 100 is illustrated in FIGS. 7-9. In particular, FIG. 7 is a side cross-section view of the wound closure device 100 being positioned in abutment with an interior surface 136 of the tissue 108 at the location of the wound 134. FIG. 8 is a side cross-section view of the deployment plate 126 being removed from the wound closure device 100, according to an example embodiment. FIG. 9 is a side cross-section view of the wound closure device 100 positioned in the abdominal cavity after the wound 134 is sewn shut, according to an example embodiment.

In particular, an example method for closing a wound 134 in a tissue 108 may include (a) positioning a wound closure device 100 into abutment with an interior surface 136 of the tissue 108 at the location of the wound 134, (b) threading a suture 106 through the tissue 108 from the interior surface 136 of the tissue 108 to an exterior surface 138 of the tissue at the location of the wound 134, and (c) applying a force to the wound closure device 100 such that at least one fixation component 104 pierces the interior surface 136 of the tissue 108, thereby affixing the wound closure device 100 to the interior surface 136 of the tissue 108. The wound closure device may correspond to any of the embodiments of the wound closure device 100 described above in relation to FIGS. 1-6.

The method may further include, prior to applying a force to the wound closure device 100 such that the at least one fixation component 104 pierces the interior surface 136 of the tissue 108, removing the deployment plate 126 from the biocompatible material 102, and bringing the adhesive material into abutment with the interior surface 136 of the tissue 108. The method may further include tightening the suture 106 of the least one fixation component 104 to thereby close the wound 134.

In one embodiment, applying a force to the wound closure device 100 such that the at least one fixation component 104 pierces the interior surface 136 of the tissue 108 includes applying tension to the suture 106 connected to and extending through the at least one fixation component 104 of the plurality of fixation components.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A wound closure device comprising:
   a biocompatible material having an inner portion surrounded by an outer portion which defines a periphery, wherein the biocompatible material is configured to be brought into abutment with a tissue surface;
   a plurality of fixation components connected to and extending through the biocompatible material, wherein each of the plurality of fixation components have a first end positioned adjacent to the biocompatible material and a second end opposite the first end, wherein the second end of each of the plurality of fixation components comprises at least one protrusion configured to penetrate the tissue surface, and wherein each of the plurality of fixation components are configured to allow a suture to be connected and extend from the second end of each of the plurality of fixation components in a direction away from each of the plurality of fixation components; and
   a rigid deployment plate removably disposed over a portion of the biocompatible material;
   wherein the plurality of fixation components are disposed on the outer portion of the biocompatible material;
   wherein the rigid deployment plate is removably disposed over the inner portion of biocompatible material such that the rigid deployment plate does not extend into the outer portion;
   wherein the rigid deployment plate is configured to shield the portion of biocompatible material covered by the rigid deployment plate from contacting the tissue surface before the wound closure device is properly positioned with the tissue surface; and
   wherein the rigid deployment plate is configured to be removed from the biocompatible material when the wound closure device is properly positioned with respect to the tissue surface such that the biocompatible material can be brought into abutment with the tissue surface to affix the wound closure device to the tissue surface.

2. The wound closure device of claim 1, wherein the biocompatible material comprises a mesh.

3. The wound closure device claim 2, wherein the mesh comprises a microreplicated mesh.

4. The wound closure device of claim 2, wherein the mesh comprises a multilayer mesh, wherein at least one layer of the multilayer mesh comprises a microreplicated material.

5. The wound closure device of claim 1, wherein the plurality of fixation components comprise a plurality of tacks.

6. The wound closure device of claim 1, wherein the at least one protrusion comprises at least one barb extending away from a body of the fixation component.

7. The wound closure device of claim 1, further comprising:
   an adhesive positioned on the biocompatible material between the rigid deployment plate and the biocompatible material to thereby removably couple the rigid deployment plate to the biocompatible material.

8. The wound closure device of claim 1, wherein the one or more fixation components in the plurality of fixation components includes an axial hole extending from the first end to the second end for accepting a suture.

9. The wound closure device of claim 1, further comprising a suture embedded in the second end of at least one fixation component of the plurality of fixation components.

10. The wound closure device of claim 1, wherein the plurality of fixation components extend through the outer portion.

11. The wound closure device of claim 10, wherein the inner portion comprises a first material, and wherein the outer portion comprises a second material that is different than the first material.

12. The wound closure device of claim 1, further comprising a suture connected to the second end of the at least one fixation component such that the suture is fixedly attached to the at least one fixation component.

13. The wound closure device of claim 1, further comprising:
   one or more vertically extending components extending away from the rigid deployment plate, wherein the one or more vertically extending components are used to pull the deployment plate off of the biocompatible material when the wound closure device is properly positioned.

14. A method of closing a wound in a tissue, the method comprising:
   positioning the wound closure device of claim 1 into abutment with an interior surface of the tissue at a location of the wound.

15. The method of claim 14, further comprising:
threading the suture through the tissue from the interior surface of the tissue to an exterior surface of the tissue at the location of the wound;
removing the deployment plate from the biocompatible material; and
applying a force to the wound closure device such that at least one fixation component pierces the interior surface of the tissue, thereby affixing the wound closure device to the interior surface of the tissue.

16. The method of claim 15, wherein at least a portion of the biocompatible material comprises an adhesive material, the method further comprising:
bringing the adhesive material into abutment with the interior surface of the tissue.

17. The method of claim 15, wherein the step of applying a force to the wound closure device such that the at least one fixation component pierces the interior surface of the tissue comprises applying tension to the suture connected to and extending through the at least one fixation component of the plurality of fixation components.

18. The method of claim 15, further comprising:
tightening the suture of the least one fixation component to thereby close the wound.

* * * * *